United States Patent [19]

Deftos et al.

[11] Patent Number: 4,837,380
[45] Date of Patent: Jun. 6, 1989

[54] LIPOSOME-CALCITONIN PREPARATION

[75] Inventors: Leonard J. Deftos; Karl Y. Hostetler, both of Del Mar, Calif.

[73] Assignee: Regents of University of California, Berkeley, Calif.

[21] Appl. No.: 26,980

[22] Filed: Mar. 17, 1987

Related U.S. Application Data

[63] Continuation of Ser. No. 781,760, Sep. 30, 1985, abandoned, which is a continuation of Ser. No. 449,053, Dec. 13, 1982, abandoned.

[51] Int. Cl.$^4$ ............................................... A61K 9/10
[52] U.S. Cl. ........................................ 424/450; 514/12; 514/808
[58] Field of Search ................... 424/450, 498; 514/12, 514/808; 264/4, 4.32; 436/829

[56]  References Cited

U.S. PATENT DOCUMENTS

| | | | |
|---|---|---|---|
| 4,186,183 | 1/1980 | Steck | 424/38 |
| 4,199,565 | 4/1980 | Fullerton | 424/89 |
| 4,235,871 | 11/1980 | Papahadjopoulos et al. | 424/38 X |
| 4,241,051 | 12/1980 | Christie et al. | 514/11 |
| 4,302,459 | 11/1981 | Steck et al. | 514/313 |
| 4,389,330 | 6/1983 | Tice et al. | 424/38 X |
| 4,416,872 | 11/1983 | Aluing et al. | 514/8 |
| 4,731,210 | 3/1988 | Weder et al. | 436/829 |

OTHER PUBLICATIONS

Williams-Textbook of Endocrinology (1974) Pub: Saunders, Phila., pp. 695-697.
Duncan's Diseases of Metabolism (Bondy et al.), Publ: Saunders, Phila. (1974), pp. 1292-1295.
Ostro-Liposomes, Publ: Marcel Nekker, N.Y. (1983), pp. 27-51.
Remington's Pharmaceutical Sciences, 15th Ed., pp. 907-908.
Hemker et al., The Lancet, pp. 70-71, Jan. 12, 1980.
Gregoriadis, New Eng. J. Med., pp. 704-710, Sep. 23, 1976.
Tragl et al., Weiner Klinische Wochenschrift, 91:448-451 (1979).
Cleland et al., J. Rheumatology, Supp. No. 5, pp. 151-163 (1979).

*Primary Examiner*—Sam Rosen
*Attorney, Agent, or Firm*—Poms, Smith, Lande & Rose

[57]  ABSTRACT

A liposome-entrapped calcitonin composition and method of use is disclosed. The composition when parenterally administerd to a host mammal, produces an enhanced and prolonged hypocalcemic effect in said mammal and thus is useful in treating diseases related to abnormal skeletal metabolism. The liposomes are substantially free of cholesterol and may be single or multilamellar.

10 Claims, No Drawings

LIPOSOME-CALCITONIN PREPARATION

This invention was made with Government support under Grand Nos. GM-24979 and AM-15888 awarded by the Department of Health and Human Services. The Government has certain rights in this invention.

This application is a continuation of application Ser. No. 06/781,760, filed Sept. 30, 1985, now abandoned, which is a continuation of application Ser. No. 06/449,053 filed Dec. 13, 1982, and now abandoned.

BACKGROUND OF THE INVENTION

1. Field of the Invention

The present invention relates to a method of achieving a biologic effect in a mammal comprising the incorporation of calcitonin into liposomes, and parenterally administering the liposome-entrapped calcitonin preparation into the body of said mammal.

2. Description of the Prior Art

Calcitonin is a polypeptide hormone secreted by the parafollicular cells of the thyroid gland in mammals and by the ultimobranchial gland of birds and fish.

Calcitonin-salmon is of salmon origin or synthetic origin, both having 32 amino acids arranged in the same linear sequence. Salmon calcitonin appears to have actions essentially identical to calcitonins of mammalian origin, but with greater potency and longer duration of action. It is presently accepted that endogenous calcitonin participates with parathyroid hormones in the homeostatic regulation of blood calcium.

Calcitonin is used in the treatment of various diseases related to abnormal skeletal metabolism (e.g. hypercalcemia, Paget's disease). Chronic therapy, however, requires daily adminisitration by parenteral injection. For that reason, it has been desired to develop new formulations so as to extend the duration of the presence of calcitonin in the tissue affected by the disease or to retain a high effective level for a long period of time by a small dose administration by intramuscular or intravenous route, thereby decreasing the frequency of administration. In addition, it has also been desired to obtain specificity with calcitonin so that it reaches its target selectively and in a controlled fashion, thereby reducing the incidence of side effects.

Liposomes have been noted as carriers for drugs, enzymes, hormones, heavy metal detoxification therapy and cancer chemotherapy in order to increase affinity of the active agents with target cells and tissues, and to alleviate their side effects. Studies have indicated that liposomes, upon parenteral injection in mammals, are taken up rapidly by cells and intracellular lysosomes of the reticuloendothelial system. Due to their relative impermeability, substances incorporated in liposomes remain concentrated and are unexposed to plasma. These characteristics suggest their suitability as carriers for calcitonin.

Liposomes are composed of phospholipids. Phospholipids have the dual characterisics of being both hydrophilic and hydrophobic at the same time. Under certain conditions phospholipids will assemble to form a double layer or bilayer. In the presence of water the bilayers form into closed spherical shapes producing the basic or simplest liposome entities. Further bilayers can be added to the basic single bilayer liposome forming concentric, closed spherical structures that range from 25 nanometers to several micrometers in diameter. The central region of the multi-layered liposome and areas between the bilayers contain water, but water is excluded from the interior, hydrophobic region of the bilayer itself. An active substance can be incorporated either into the aqueous or non-aqueous regions.

Generally, two techniques are used for incorporation of an active substance in lipsome. One technique involves dissolving the appropriate lipids in an organic solvent, which is subsequently removed, leaving behind a thin film. The substance to be incorporated is added to the film in water; the film dispersed on shaking forms individual liposomes with the entrapped substance. The other technique involves the use of lipid-soluble active substances which are dissolved together with the lipids.

SUMMARY OF THE INVENTION

In accordance with the present invention calciitonin is entrapped in liposomes and the liposome-entrapped calcitonin is introduced into the body by parenteral administration, thereby producing a biologic effect. As specific embodiment of the invention, the use of liposome-entrapped calcitonin has been found to produce a more prolonged and greater reduction in serum calcium in a mammal when compared to parenteral administration of non-liposome-entrapped calcitonin. Such an invention could be useful in the treatment of various skeletal-related diseases such as hypercalcemia, Paget's disease and osteoporosis.

Incorporation of calcitonin in liposome comprises: dissolving the lipids in an organic solvent; removing the solvent to obtain a liposome film; adding to said lipid film a solution containing calcitonin; mixing the solution with the lipid film to form a suspension; sonicating the suspension to form liposome-entrapped calcitonin; centrifuging the suspension to obtain a supernatant containing liposome-entrapped calcitonin and unentrapped or free calcitonin; applying the supernatant to a chromatographic column; and eluting the entrapped and unentrapped calcitonin from the column with a trapping buffer solution.

The phospholipids used in accordance with the present invention may be of both natural or synthetic origin and include, for example, phosphatidylcholine, sphingomyelin, dimyristoylphosphatidylcholine and dioleoylphosphatidylcholine.

In another embodiment of the invention cholesterol can be used along with phospholipids for the entrappment of calcitonin using the herein-described procedure.

Both natural and synthetic origin calcitonin may be used for incorporation in liposome; the percentage of calcitonin entrapped in liposome can range from about 10 to 30% of the total recovered calcitonin while the ratio of lipid to calcitonin in the preparation may vary.

The organic solvents used to dissolve the lipid may be a single solvent, such as chloroform or methanol or mixtures thereof. Other organic solvents that may be used include ethanol, methanol and the like.

The buffer used for preparing liposome-entrapped calcitonin preferably is 20 mM NaCl containing about 5 mM Tris (hydroxymethyl) aminoethane and having a pH of about 7.4.

The preferred chromatographic column for the separation of liposome-entrapped calcitonin is Sepharose 4B sold by Pharmacia, Fine Chemicals, Piscataway, N.J. However, other chromatographic columns may also be used.

Liposome-entrapped calcitonin preparations of the present invention showed a 2 to 5 fold increase in hypocalcemic activity as compared to hypocalcemic activity of free calcitonin.

Other aspects of the present invention will be better understood and more appreciated upon reading the following detailed description of the invention.

DETAILED DESCRIPTION OF THE INVENTION

EXAMPLE I

Fifty micromoles of egg phosphatidylcholine (eggPC; Sigma, St. Louis, Mo.) was dissolved in chloroform/methanol (1:1, v:v). The material was placed in a 20×100 mm pyrex tube with tapered glass stopper and the solvents were removed in vacuo. One ml of trapping buffer (20 mM NaCl containing 5 mM Tris, pH 7.4) containing human calcitonin (Armour Pharmaceutical Co., Kankakee, Ill.) and its radioiodinated tracer was added and the contents of the tube was mixed (Vortex) for 5 minutes. The suspension was sonicated in a cuphorn (Sonicator cell disruptor, Model W185 Fi, Heat System-Ultrasonics, Inc.) for 3 minutes. The preparation was then centrifuged at 8,500×G for 5 minutes at 4C° and the supernatant was applied to a 2.5×64 cm column of Sepharose 4B (Pharmacia, Fine Chemicals, Piscataway, N.J.) and eluted with trapping buffer in order to separate free calcitonin (F-CT) from liposome-entrapped calcitonin (L-CT). Both F-CT and L-CT were eluted with the trapping buffer with the F-CT being eluted last. The separation was monitored by measuring the radioactivity of $^{125}$I-CT or by specific radioimmunoassay.

For radioimmunoassay measurements both F-CT and total CT were measured. The latter was accomplished by first disrupting the liposomes with 0.05% Triton X-100 to release the CT. Standard curves were done both in buffer and in buffer containing 0.05% Triton X-100. Thus, L-Ct could be calculated by subtracting F-CT from total CT. The liposome-CT preparation was stored at 4C°. The stability of this preparation was evaluated by its biological effect periodically up to 4 weeks after preparation. The phosphate concentration of the liposomes was also determined.

EXAMPLE II

The same procedure and materials were used as in Example I, except that sonication of the suspension continued for a total of 20 minutes.

EXAMPLE III

The same procedure was used as in Example I, except that in addition to using 50 micromoles of egg phosphatidylcholine, 50 micromoles of cholesterol (Sigma, St. Louis, Mo.) was also added.

EXAMPLE IV

The same procedure was used as in Example III, except that sonication of the suspension continued for a total of 20 minutes.

EXAMPLES V–VIII

Procedures described in Examples I–IV were used to entrap salmon-calcitonin.

In examples I, III, V and VII, the 3 minutes sonication resulted in essentially equal amounts of large multilamellar vesicles (MLV) and small unilamellar vesicles (SUV), while in Examples II, IV, VI and VII, the 20 minutes sonication resulted in a small amount of MLV and a large amount of SUV. The percentage of calcitonin entrapped in liposome ranged from 16 to 22% of the total recovered $^{125}$I-CT,

EXAMPLE IX

The compositions of Examples I–VIII were tested in animals as follows.

Eighty to 100 g male rats of the Fischer 344 strain were fasted overnight. Liposomal-entrapped (L-CT) and non-entrapped or free (F-CT) calcitonin were administered at different doses by the intravenous or intramuscular route under methoxyflurane anesthesia. Blood samples were collected serially for calcium (Ca) measurement. The biological effect of the different CT preparations was determined by measuring changes in the calcium concentration of rat serum with a Corning Calcium Analyzer (Corning, Model 9940). The potency of the CT preparations was calculated on the basis of the change in serum Ca alone as well as by summating the effects on change in serum Ca at sequential time points. The doses used in these studies were 0.047 units (u) of human CT per 100 g body weight and 1.9 units (u) of salmon CT per 100 g body weight. The data shown represent the means of replicate determinations for which the coefficient of variation was less than 10%.

Table I shows the results of intravenous administration of various liposome preparations containing human calcitonin in rats wherein: the numbers indicate a decrease in serum calcium expressed in arbitrary units; $ePC_{50}C_0MLV$ = egg phosphatidycholine-(50 μ moles, cholesterol (0 μ moles)-calcitonin, large multilamellar vesicles; SUV denotes small unilamellar vesicles. The remaining preparations are denoted similarly.

TABLE I

| Liposome-preparations | INTRAVENOUS ADMINISTRATION | | | | |
|---|---|---|---|---|---|
| | Time = | | | | |
| | 1.17 hr | 4.5 hr | 8 hr | 23 hr | Summated |
| $ePC_{50}C_0$ MLV | 1.91 | 0.91 | 0.76 | 0.78 | 4.36 |
| $ePC_{50}C_0$ SUV | 1.28 | 0.21 | 0.28 | 0.01 | 1.78 |
| $EPC_{50}C_{50}$ MLV | 0.85 | 1.05 | 0.81 | 0.56 | 3.27. |
| $EPC_{50}C_{50}$ SUV | 0.01 | 0.42 | 0.35 | −0.28 | 0.50 |

With cholesterol-free liposomes ($ePC_{50}C_0$) the maximal decrease in serum Ca was observed at about 1 hr 17 min. for both multilamellar (MLV) and small unilamellar (SUV) vesicles entrapped human calcitonin. However, when the liposomes contained cholesterol ($ePC_{50}C_{50}$) the maximal fall in serum Ca occured at about 4.5 hours. MLV-entrapped calcitonin was more effective than SUV-entrapped calcitonin regardless of the presence or absence of cholesterol. The cholesterol-free MLV-entrapped human calcitonin was the most effective among the above-shown preparations.

Table II shows the results of intramuscular administration of various liposome preparations containing human calcitonin in rats wherein the notations have the same meaning as in Table I.

TABLE II

| Liposome preparation | INTRAMUSCULAR ADMINISTRATION | | | | |
|---|---|---|---|---|---|
| | Time = | | | | |
| | 1 hr | 3 hr | 6 hr | 24 hr | Summated |
| $ePC_{50}C_0$ MLV | 1.40 | 1.73 | −0.06 | 0.08 | 3.15 |
| $ePC_{50}C_0$ SUV | 2.21 | 1.97 | 0.68 | −0.01 | 4.85 |
| $ePC_{50}C_{50}$ MLV | 0.10 | 0.21 | 0.29 | 0.24 | 0.84 |
| $ePC_{50}C_{50}$ SUV | −0.20 | 0.20 | 0.19 | 0.22 | 0.41 |

It can be discovered from the table that niether MLV or SUV liposomes containing human calcitonin were effective in lowering serum Ca in the presence of cholesterol (ePC$_{50}$C$_{50}$). While both cholesterol-free MLV and SUV liposome-entrapped calcitonin are effective in producing a substantial drop in serum Ca 1 to 3 hrs after injection, SUV liposome-entrapped calcitonin is the more effective between the two preparations.

As shown in Tables III and IV, hypocalcemic activity of liposome preparations of the present invention containing both human (hCT) and salmon calcitonin (sCT was compared with the activity of an equivalent dose of the respective free calcitonin. For the intravenous studies (Table III) the liposome used was ePC$_{50}$C$_0$MLV; for the intramuscular studies ePC$_{50}$C$_0$ SUV was used (Table IV).

TABLE III

| INTRAVENOUS ADMINISTRATION | | | | |
|---|---|---|---|---|
| | Time = | | | |
| Preparation | 1 hr | 3 hr | 6 hr | Summated |
| MLV liposome-hCT | 1.76 | 1.52 | 0.49 | 4.17 |
| free hCT | 0.79 | 0 | 0 | 0.79 |
| MLV liposome-sCT | 1.91 | 2.34 | 2.61 | 6.86 |
| free sCT | 1.71 | 2.22 | 1.997 | 5.90 |

TABLE IV

| INTRAMUSCULAR ADMINISTRATION | | | | | |
|---|---|---|---|---|---|
| | Time = | | | | |
| Preparation | 1 hr | 3 hr | 6 hr | 9 hr | Summated |
| SUV liposome-hCT | 1.80 | 2.20 | 0.07 | 0.20 | 4.27 |
| free hCT | 1.47 | 0.03 | 0.18 | 0.05 | 1.73 |
| SUV liposome-sCT | 1.80 | 2.72 | 3.00 | 2.71 | 10.23 |
| free sCT | 1.86 | 2.08 | 0.39 | 0.18 | 4.51 |

As shown, liposomal entrapment of both human calcitonin and salmon calcitonin enhanced the hypocalcemic effect and delayed the peak effect.

While the mechanism of liposome-entrapped calcitonin producing increased hypocalcemic effect, as compared to free calcitonin, is not well understood, it is theorized that at least in the case of intravenous injections of liposome-entrapped calcitonin local leakage of entrapped materials may occur during adsorption of fusion of liposomes with the plasma membrane. This leakage may result in high local concentration of calcitonin near the plasma membrane and calcitonin receptors of target cells causing the hypocalcemic effect. However, in the case of intramuscular injections, direct interactions of liposomes with the surface of target cells seem less likely since these liposomes probably do not gain direct excess to the circulation.

Having described the invention, those skilled in the art will be able to make modifications within the spirit thereof, and the invention is to be limited only within the scope of the appended claims.

What is claimed is:

1. A liposome-entrapped preparation for parenteral administration into mammals to produce a rapid maximal decrease of serum calcium comprising an effective amount of calcitonin encapsulated in a vesicle consisting essentially of a cholesterol-free phospholipid, parenteral vehicle.

2. A liposome-entrapped preparation according to claim 1 wherein said calcitonin is selected from the group consisting of human calcitonin, salmon calcitonin and synthetic calcitonin.

3. A liposome-entrapped preparation according to claim 1 wherein said vesicle is a multilamellar vesicle.

4. A liposome-entrapped preparation according to claim 1 wherein said vesicle is a unilamellar vesicle.

5. A liposome-entrapped preparation according to claim 1 wherein said phospholipid is selected from the group consisting of phosphatidylcholine and dioleoylphosphatidylcholine.

6. A liposome-entrapped preparation according to claim 5 wherein said phospholipid is egg phosphatidylcholine.

7. A liposome-entrapped preparation according to claim 6 wherein said vesicle is a multilamellar vesicle.

8. A method of producing an increased and prolonged hypocalcemic effect in a mammal comprising: parenterally administering into said mammal an amount of the composition of claim 1 which is effective to produce a hypocalcemic effect.

9. A method according to claim 8 wherein said administration is intravenous.

10. A method according to claim 8 wherein said administration is intramuscular.

* * * * *